(12) United States Patent
Norton

(10) Patent No.: US 6,880,414 B2
(45) Date of Patent: Apr. 19, 2005

(54) SORT BLOCK AND LIQUID COLLECTION DEVICE FOR SORTING FLOW CYTOMETER

(75) Inventor: Pierce Norton, Morgan Hill, CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 392 days.

(21) Appl. No.: 10/215,971

(22) Filed: Aug. 8, 2002

(65) Prior Publication Data

US 2004/0025602 A1 Feb. 12, 2004

(51) Int. Cl.[7] ............................................... G01N 29/00
(52) U.S. Cl. ................................................... 73/865.5
(58) Field of Search .............................. 73/865.5, 28.02; 324/71.4; 356/440, 441, 437; 436/63, 164; 422/73, 82.05; 382/133; 209/3.1, 577, 579, 906

(56) References Cited

U.S. PATENT DOCUMENTS

| | | | |
|---|---|---|---|
| 4,844,610 A | 7/1989 | North, Jr. ...................... 356/73 |
| 5,483,469 A | * 1/1996 | Van den Engh et al. ...... 702/21 |
| 5,776,781 A | * 7/1998 | Vardanega et al. ............ 436/63 |
| 6,079,836 A | 6/2000 | Burr et al. ..................... 357/70 |
| 6,248,590 B1 | * 6/2001 | Malachowski ................ 436/63 |
| 6,281,018 B1 | * 8/2001 | Kirouac et al. ............... 436/63 |
| 6,372,506 B1 | * 4/2002 | Norton ......................... 436/63 |
| 6,524,860 B1 | * 2/2003 | Seidel et al. .................. 436/63 |

FOREIGN PATENT DOCUMENTS

WO   WO01/68226    9/2001
WO   WO01/85088    11/2001

OTHER PUBLICATIONS

I. Schmid et al., "Biosafety Guidelines for Sorting of Unfixed Cells", Cytometry, 28, pp. 99–117, 1997.
R.G. Ashcroft et al., "Commercial High Speed Machines Open New Opportunities in High Throughput Flow Cytometry (HTFC)", J. of Immunological Methods, 243, 2000, pp. 13–24.

* cited by examiner

Primary Examiner—Robert Raevis
(74) Attorney, Agent, or Firm—Douglas A. Petry

(57) ABSTRACT

A sort block for use with sorting flow analysis system. The sort block includes a fin extending into a sort stream in the sort block. Unsorted particles and aerosol are aspirated into the open top of the fin. When error is detected, collection baskets associated with the fin extend into the sort stream, block passage of particles to the collection containers and aspirate all droplets and aerosol to a waste or retrieval container. This sort block may include error monitors, such as a laser and camera combination, which monitor the flow stream and control the extension of the fin and basket type collector.

27 Claims, 8 Drawing Sheets

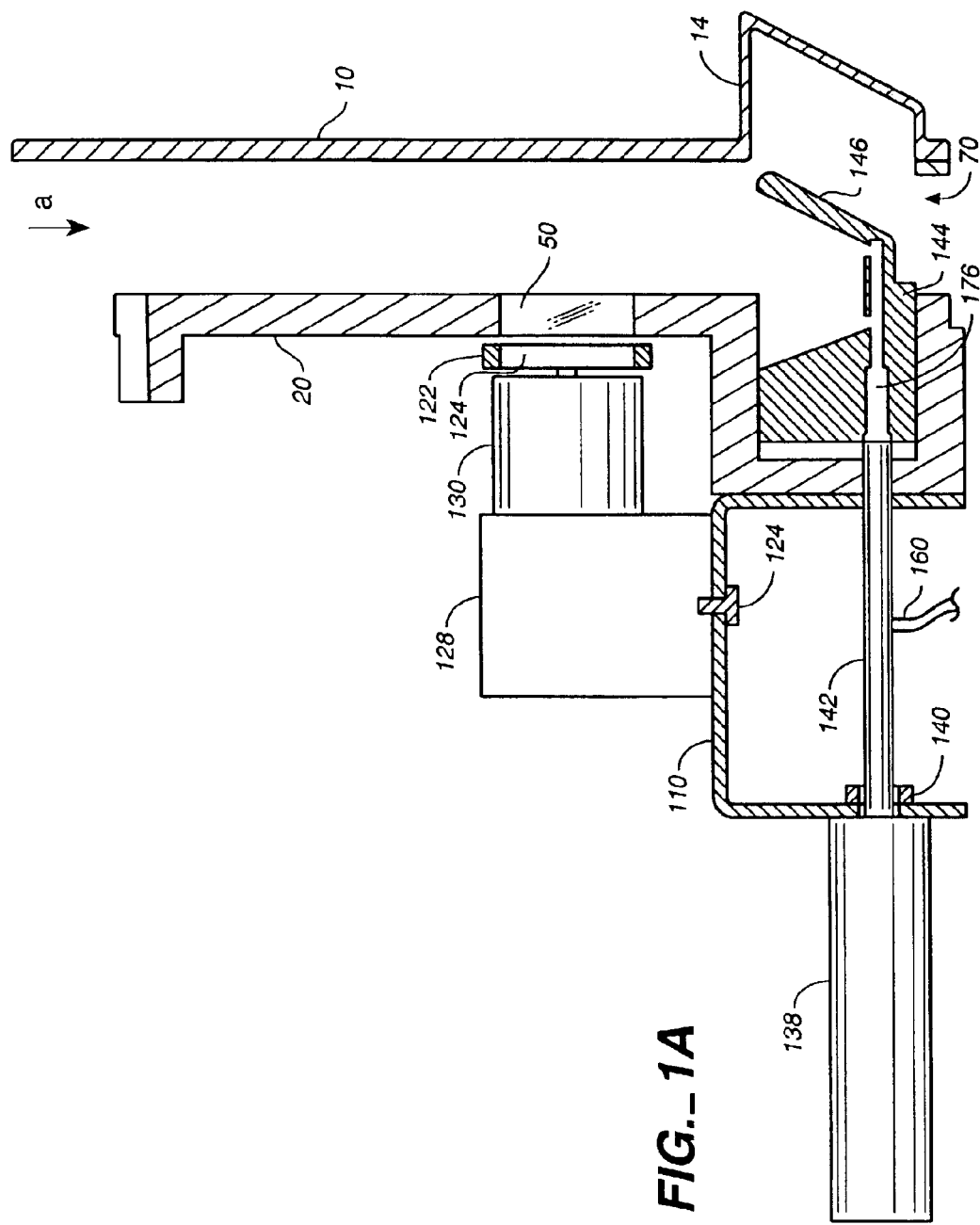
FIG._1A

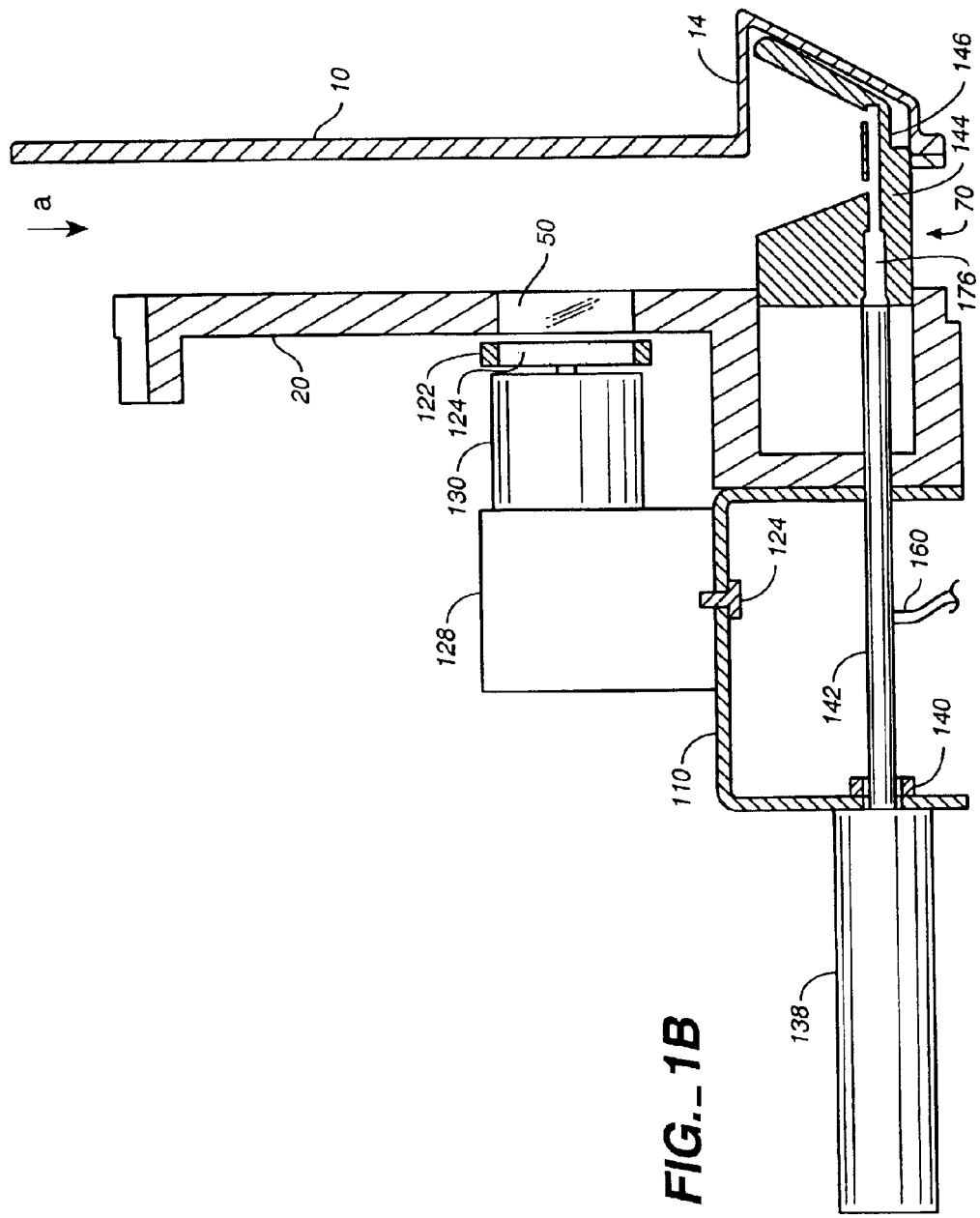
FIG._1B

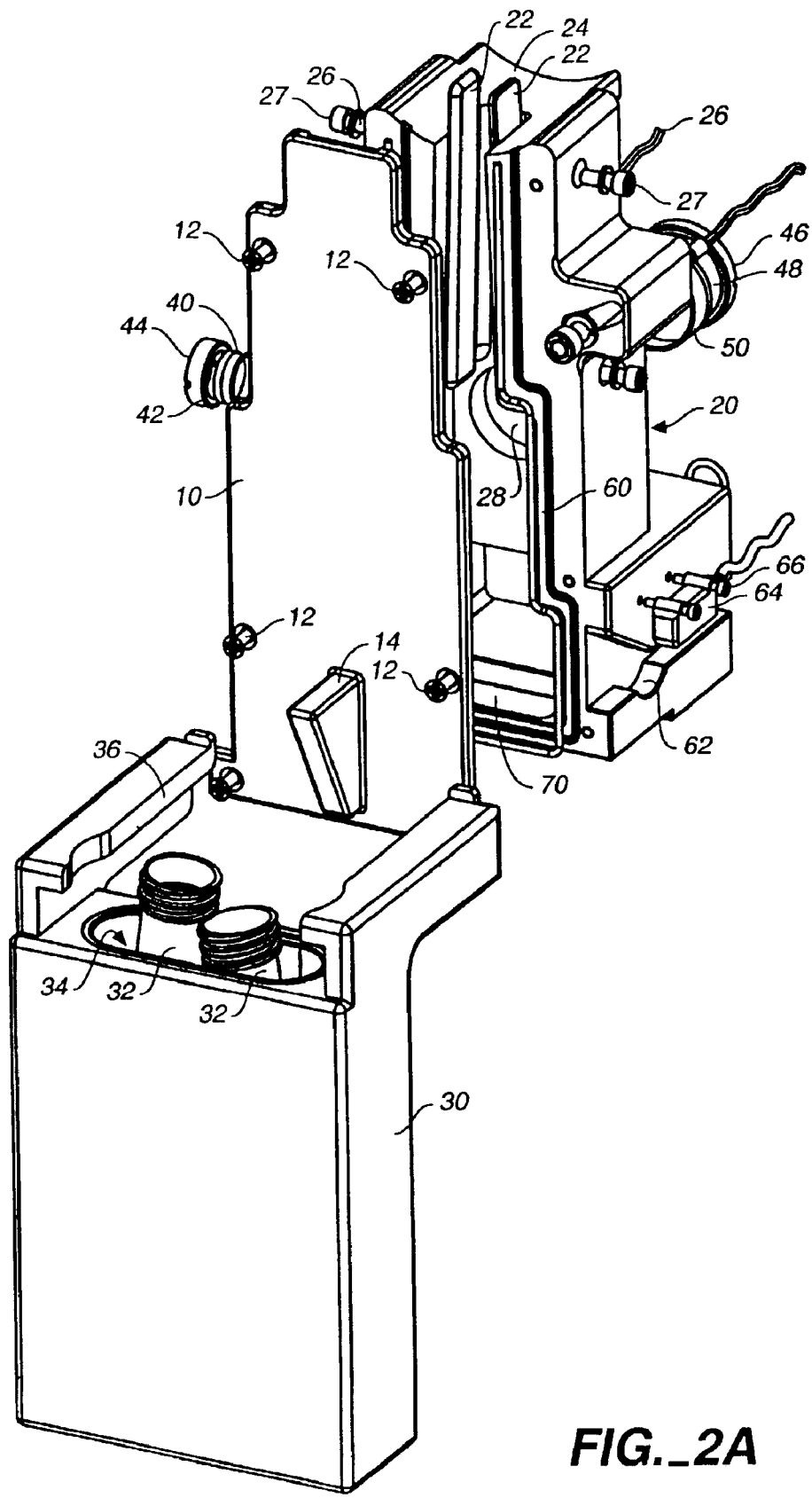
FIG._2A

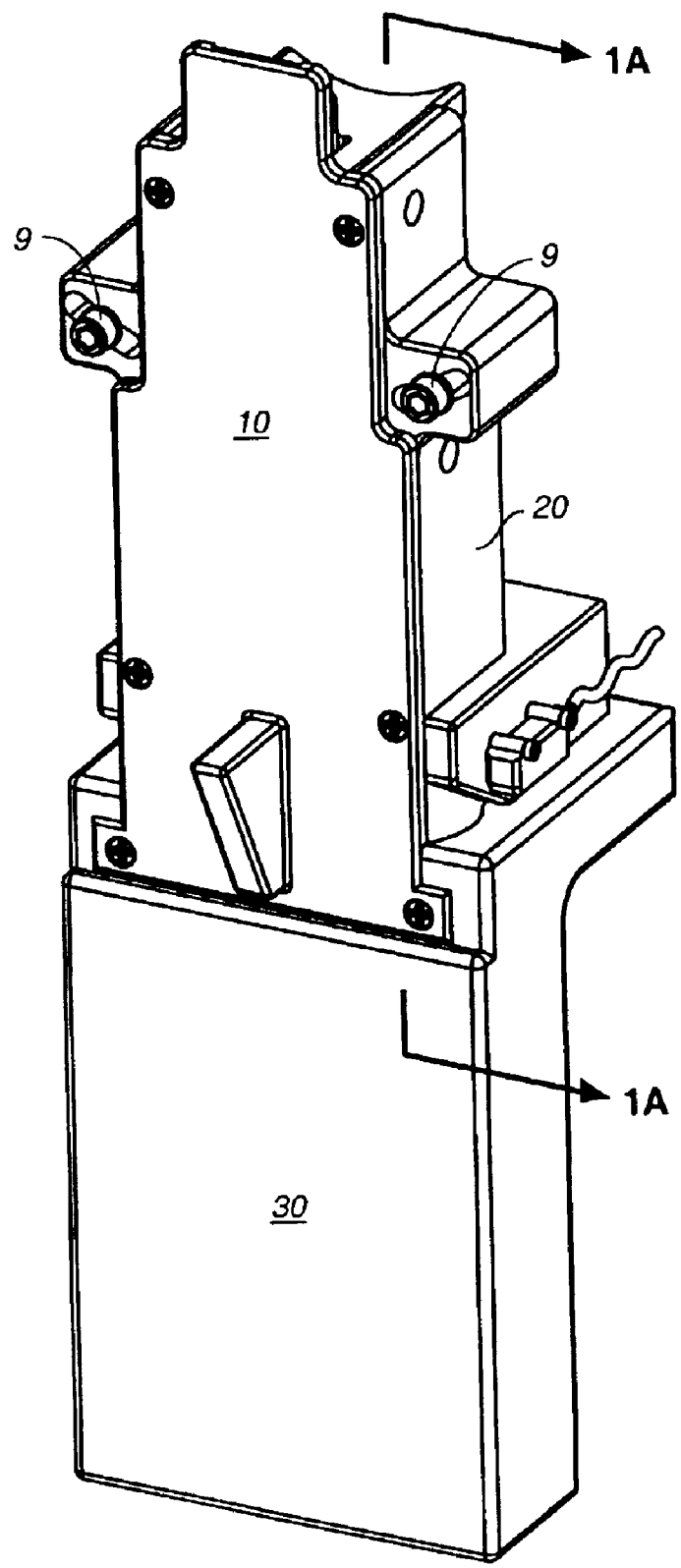
FIG._2B

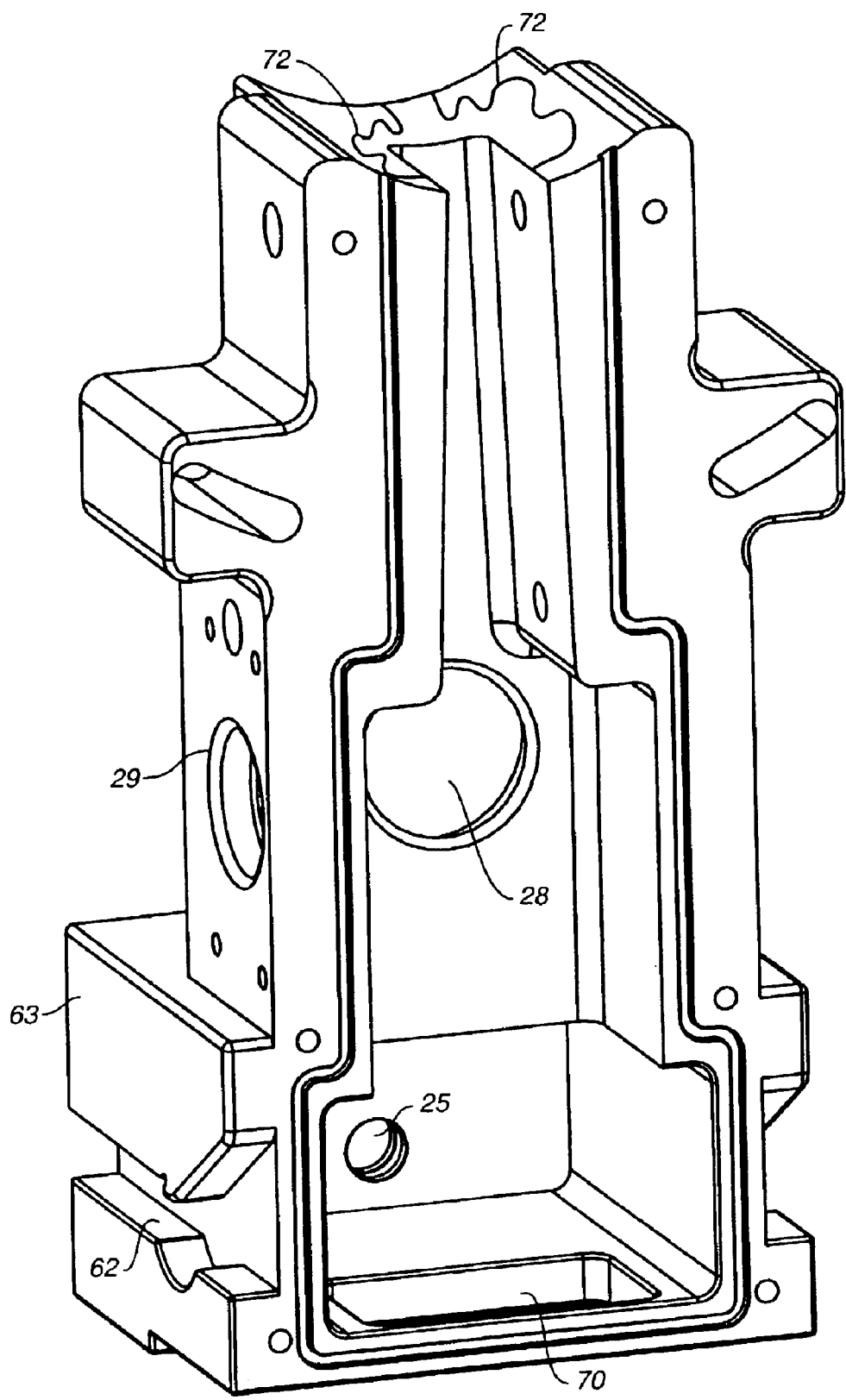
FIG._3

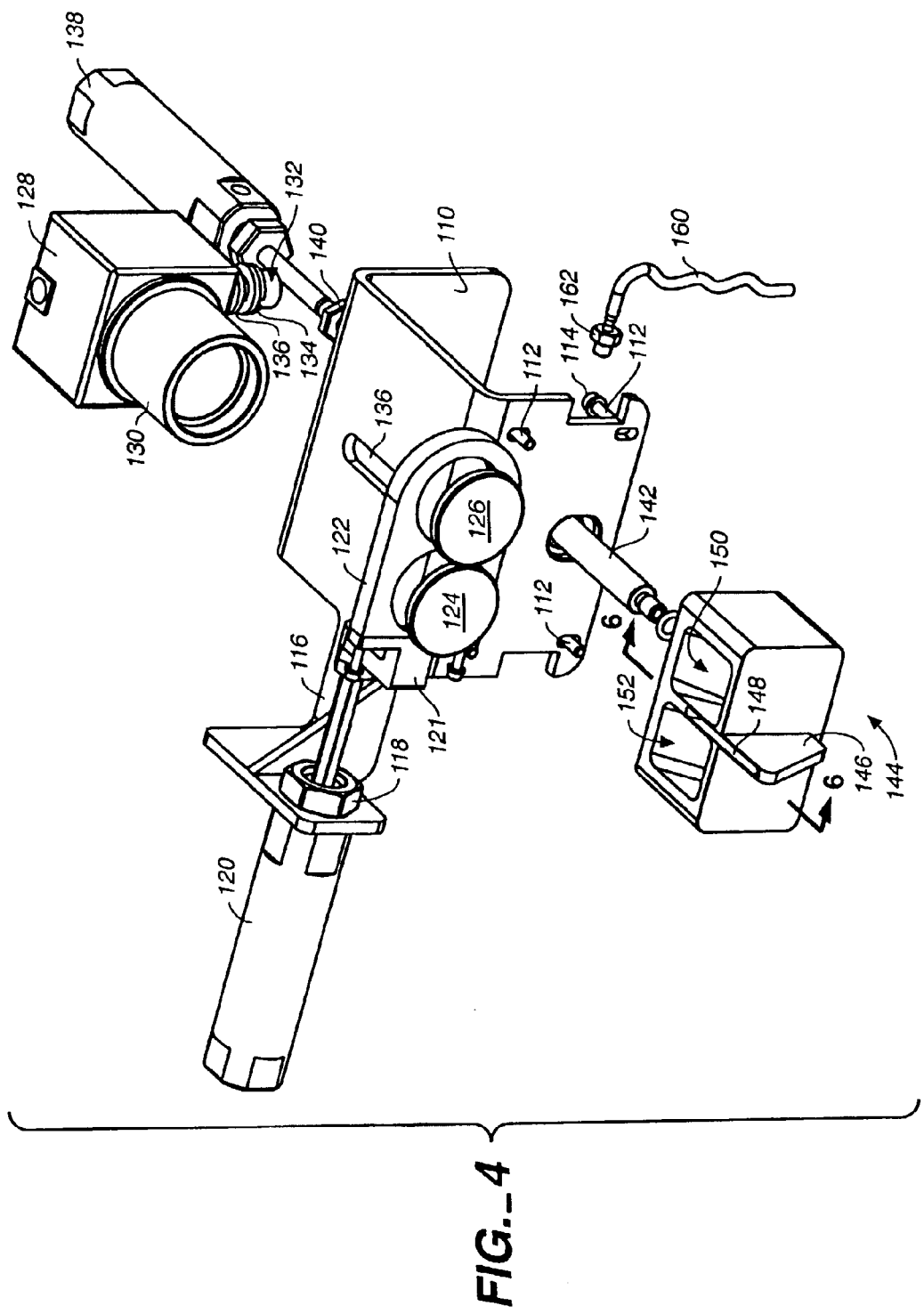
FIG._4

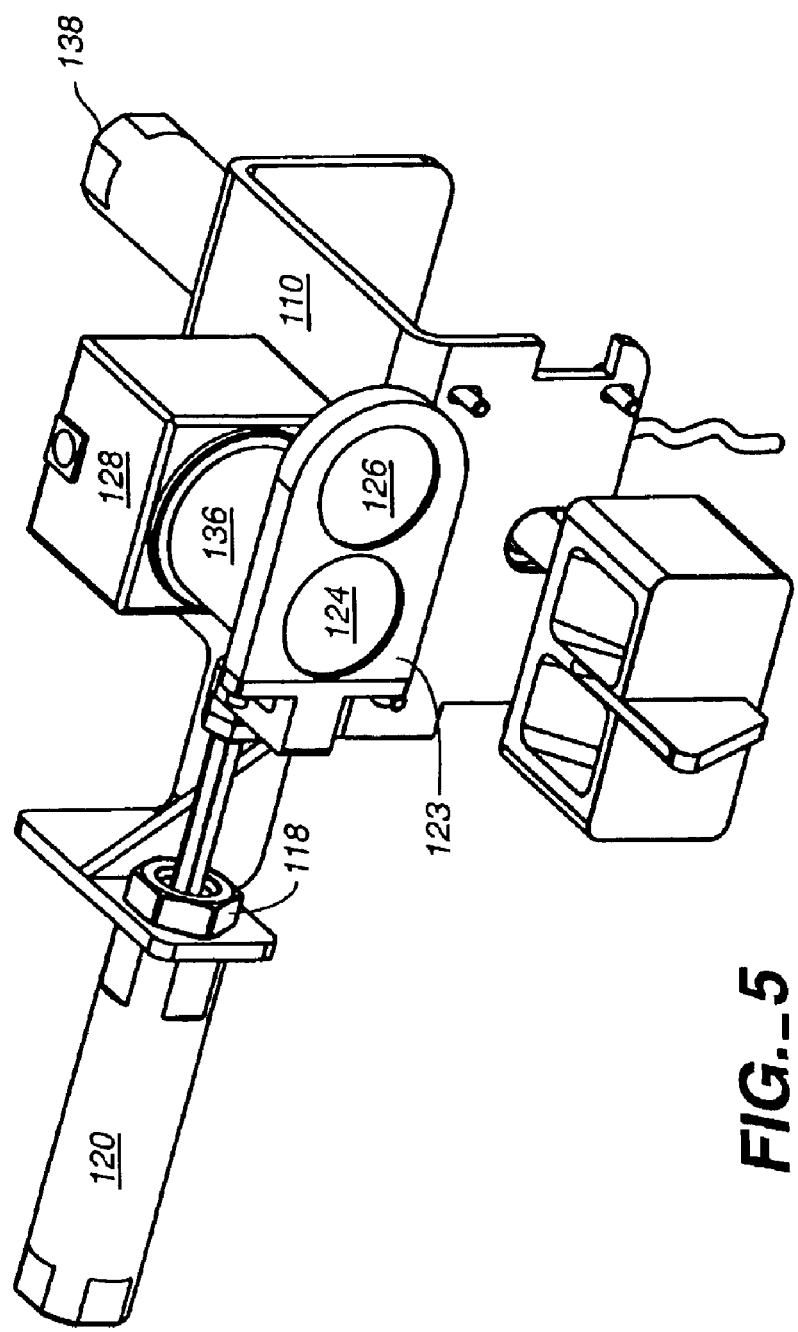
FIG._5

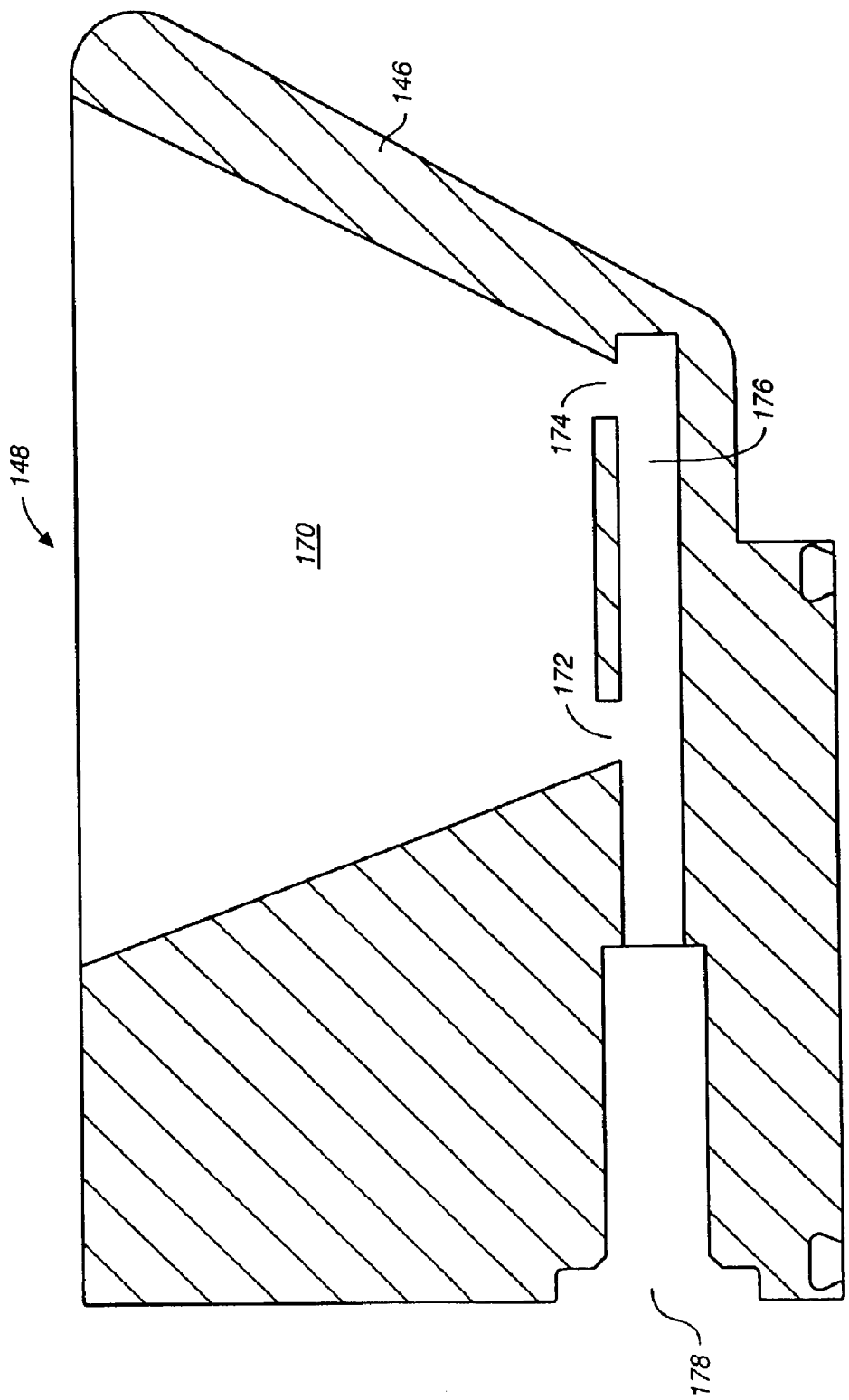

SORT BLOCK AND LIQUID COLLECTION DEVICE FOR SORTING FLOW CYTOMETER

TECHNICAL FIELD

This invention relates generally to flow cytometer systems. More specifically, the invention relates to an improved system for particle collection to ensure safety through aerosol collection while preserving sort integrity by allowing interruption of particle flow to collection containers in instance of error.

BACKGROUND OF THE INVENTION

Flow cytometers are frequently used for the analysis of particles such as cells or beads in a number of different applications. The system allow for determination of both particle morphology and evaluation of particle features by detection of optical labels. The ability to distinguish multiple particles sizes and colors allows multiplex application providing higher capacity of this technology to obtain information from analyzed targets.

Particle as used herein means any discrete target that may be optically analyzed, enumerated or sorted by a flow cytometer. This group includes cells, cell fragments and beads.

In flow cytometer systems liquid containing target particles are fed from a container into a flow cell. The flow cells separates particles into a stream of individual particles that flow past a detection location. The particles may flow as individual droplets, but to reduce optical noise from refraction it is often preferred to have the particle stream flow through a cuvette where particles in the flow stream are analyzed. At the detection location a beam of focused illumination light (often a laser beam) illuminates the passing particles.

Light scattered by the passing particles is detected by forward and side scatter detectors allowing determination of particle morphology. Light emitted from particles is collected and transmitted to detection optics. The particle (generally a cell or bead) may be labeled with one or more dye having a characteristic excitation and fluorescent emission wavelength. The dye may be conjugated to a binding agent (e.g. a monoclonal antibody) allowing targeting of specific antigen associated with the bead or cell. Light beam splitters separate the collected light into component wavelengths. These beams are directed through a bandpass filter to a light detector (e.g. photomultiplier tube). A specific wavelength associated with each dye is individually detected by one detector.

The particle, after passing through a flow cell may pass into a sorting block for cell sorting operations. The flow cell nozzle breaks the flow stream into individual droplets, each droplet potentially containing one or more particle. If the particle is to be collected, the droplet is given a charge by a charging system. The droplets then fall in a stream past charged deflection plates in the sort block. Charged droplets will be deflected in one of two directions, depending on the charge applied to the droplet. The uncharged droplets are not deflected and may be collected as unsorted particles. The charged droplets are deflected and exit the sort block to collection containers. If the particles are cells, the sorted cells may then be used for additional procedures. By applying different levels of positive or negative charge a single sort procedure may sort the flow stream into four containers.

There are a number of potential problems with cell sorters. First, if the sorter malfunctions particles could be sprayed as an aerosol through the sort block. The sorted particles in containers would be contaminated and need to be resorted. Such a malfunction could include a block in the flow cell resulting in the flow stream being aerosoled into a fine mist through the sort block. In addition, pressure changes could result in spraying from the sort nozzle. Alternatively, error in the charging system could also misdirect particles. This spraying malfunction would result in the contamination of sorted particles, potentially wasting hours of sorting time. The repeated sorting of cells may also negatively affect cell vitality and viability.

A second potential problem is the aerosols generated by the sort nozzle. The particles are sorted into droplets that fall to the container. The particles are of sufficient size that the flow direction and the droplet weight act to draw the droplet to the sort containers or into a collector for unsorted cells. However in the formation of droplets some fluid may form an aerosol in the sorting block. The aerosol is composed of a fine mist that can be suspended in the air in the sort block. An aerosol could escape the sort block if it is not airtight and expose the user to the aerosol. This can be hazardous, especially given that sorting of blood cells is a common flow cytometry procedure. A virus, such as HIV or the Hepatitis virus, could escape the sort block in an aerosol. The flow cytometer user could then be exposed to this virus. If radioactive agents are used, exposure of the user to radioactive agents would also pose hazard from aerosols generated.

The potential hazards are evaluated in Cytometry 28:99–117(1997). The recommendations for safety noted in this publication include decontamination of an instrument with a disinfecting agent following use, a vacuum containment system on the sorter to remove aerosols (while ensuring that air turbulence is not created in the sort stream), removal of unsorted cells to a waste stream, and enclosure of the sort system in a housing to prevent aerosol escape. This housing has generally contained the flow cell and sort block, containing all elements in an enclosed chamber to prevent aerosol escape. The housing may then be evacuated with a vacuum following a sort process, ensuring that any aerosol generated is evacuated through a filter cartridge.

Most flow cytometers rely on manual shut off to prevent system error. However, in the time required to shut off the flow system, a sorting process could be ruined. If a containment housing is used, the housing must be evacuated and sterilized and the sort repeated.

U.S. Pat. No. 5,776,781 discloses a system for isolation of flow cytometer elements to enclose the system and prevent the escape of aerosols. In addition, the system has a component to sterilize the enclosed area using a chemical or UV light sterilizer. The system maintains positive pressure within the isolation chamber to maintain sterility and ensure that particles from outside the isolation chamber do not gain entrance. The isolation chamber encloses the flow cell, droplet generator, charging system, deflecting system and cell collector. As in other systems, a significant volume of space must be enclosed, adding bulk to the system. Additional lab space is required for such large systems.

PCT document WO 01/85088 A1 discloses a safety cabinet for use with a flow cytometer. The flow cytometer is enclosed within the cabinet. A blower/filtration means removes and filters air from the cabinet, maintaining negative pressure within the cabinet.

U.S. Pat. No. 6,248,590 discloses a system in which a flow interrupter is brought into the flow stream to divert the entire flow stream in instances where an optical stream evaluation system determines that some required parameter is not satisfied. The stream is then shunted to waste by a deflector or gutter introduced into the flow area.

Past devices have achieved a safer containment at the cost of system bulk. The aspirators employed to maintain a negative air pressure within the sorting block would have to provide enough pressure to evacuate the contained area which may be a sizeable volume. In addition a robust system for protecting cells that have been sorted from sprays resulting from malfunction is not presently available.

It is an object of the present invention to provide a flow cytometer sort block that provides a means for detecting system error and collecting the entire flow stream and shunting the flow stream from the collection containers. This would prevent the collected cells or beads from being contaminated.

It is a further object of the invention to provide a sort block that prevents aerosol escape.

It is a further object of the invention to provide a means for introducing negative pressure within the sort block.

SUMMARY OF THE INVENTION

The above objects have been achieved with a new sort block having features to enhance safety and protect sorted cells from contamination.

In one embodiment, a cell sort block is comprised of a block body and a block face attached together to define a sort chamber with an open end at the top and bottom. An O-ring may be present along the edge of the face to ensure a tight seal of the block face to the block body.

The sort block is designed such that a flow cell, sort nozzle and charging system may be mounted at the top of the sort block. These elements are mounted with a seal such that there is no leakage of air from these components. A circuitous air intake may be patterned into the top of the sort block to allow some air to enter the sort block. This air would replace air evacuated from the chamber by an aspiration system.

The flow cell optically interrogates particles as the particles pass a detection window. Scattered light and emitted fluorescent light is collected and detected by the flow cytometer. The flow stream flows through the flow cell into the droplet-generating nozzle.

The nozzle generates a particle stream, generally comprised of individual cells or beads in individual droplets, which pass through the sort chamber to the open bottom end. Specified particles of interest may be charged with the charging system after the droplets have been formed.

The particles flow through the sort block in a stream. A particle deflector (e.g. electrostatic charging plates) deflects targeted particles that have been charged by the charging system. The direction and degree of deflection depends on the strength of the charge and whether the charge is positive or negative. At present a flow stream can be deflected in one of four paths (two streams on each side of a central stream of undeflected droplets). The central stream of droplets are not charged or deflected and maintain their original trajectory.

In the sort chamber, between the deflection plates and an open bottom end of the sort block, is positioned a multipurpose device for aspiration of aerosols, collection of unsorted particles and flow interruption in case of error. This devices is comprised of a fin with an open top and an closed bottom extending into the flow stream such that unsorted (i.e. undeflected particles) are collected into the open top. Flanking the fin are two collection baskets on either side of the fin. The fin extends into the sort chamber beyond the two baskets. The fin and basket device is mounted on an actuator arm of an actuator. During a sort, the actuator is in a retracted position such that the fin extends into the sort stream but the baskets do not. An aspirator is associated with the fin such that an aspiration force is channeled through a cavity in the fin. Aerosol generated by the droplet formation is collected into the fin by the aspiration force without detrimentally altering the trajectory of the droplets to be collected. An air intake near the top of the sort block allows air to flow into the chamber to replace air evacuated by the aspirator.

When an error is detected the actuator is activated and extends an arm attached to the particle collector such that both the fin and the baskets are positioned in the sort stream. Both deflected and non-deflected droplets are collected. The collected droplets are removed by the aspirator to an aspirator line. The particles are collected into a container and may be subsequently resorted. By extending the actuator and moving the collection baskets into the stream of the deflected particles, the particles already collected into collection containers remain uncontaminated. A number of different error sensing systems, including optical system, pressure sensing systems, computer error sensing systems and electrical monitoring systems may be used to detect system error.

BRIEF DESCRIPTION OF THE DRAWINGS

FIG. 1A is a cross section of a sort block, camera, and aspiration/collection device with the device retracted.

FIG. 1B is the cross section of FIG. 1A with the aspiration/collection device extended.

FIG. 2A is an exploded view of the sort block and container holder of FIG. 1.

FIG. 2B is a perspective view of the sort block and container holder of FIG. 2A.

FIG. 3 is a perspective view of the sort block.

FIG. 4 is an exploded view of the optical flow monitoring and aspiration/flow stream collection systems.

FIG. 5 is a perspective view of the systems of FIG. 4.

FIG. 6 is a cross section of the fin of the aspiration/flow stream collection device.

DETAILED DESCRIPTION OF THE INVENTION

In the present description, the components of the system are first described followed by a description of a system cross section illustration of the components in combination. With reference to FIG. 2A, the particle sort block is comprised of block body 20, block face 10, and container holder 30. Block face 10 may be secured to block body 20 by screws 12. In one embodiment, an O-ring 60 is disposed along two sides and the bottom of sort block body 20. O-ring 60 is proximate to the edge of block face 10. Block face 10 may be made of a transparent material to allow the user to monitor the flow stream. This allows the face to be sealed such that even fine aerosol could not escape from the enclosed sort chamber. Container holder 30 may be held in position on sort block body 20 by holder slide rail, which seats on sort block rail 62. In FIG. 3, the top slide rail 63 and bottom slide rail 62 are shown. Top slide rail 63 has a retaining latch to secure the rail on the container holder in place. In FIG. 2B, the sort block with attached collection container holder is shown. Face 10 is secured onto sort block body 20. Container 30 is fit onto block body 20.

Bolts 9 may be used to mount he sort block on a frame. These bolts would allow some angular adjustment of the sort block positions. In flow cytometer systems, aligning the sort block with the flow stream is needed to allow particle sorting. The stream of droplets should be centered between the deflection plates. To ensure this alignment a flow cytometer may allow redirection of the droplet stream relative to the sort block. In a number of present sort systems, the flow cell or sort nozzle is mounted on an x-y-z stage to allow targeting of the sort stream in three dimensions. The flow cell mount may also allow α and θ angular rotation. This targeting of the flow cell or sort nozzle ensures the sort stream is properly directed to collection containers.

However, if the sort nozzle is part of a fixed position flow cell cuvette a different means is needed to align the droplet stream relative to the sort block. In one embodiment of the present device bolts 9 are used for this alignment, ensuring that the droplet streams flow to the collection containers and that the drop stream is centered between deflection plates. As seen in FIG. 2B, bolts 9 extend through sort block body 20. Bolts 9 may be secured to a frame of a flow cytometer. Bolts 9, when tightened, secure the sort block in a fixed position. If the flow stream is angled slightly, bolts 9 may be loosened and the sort block repositioned. The elongate holes through which bolts 9 are inserted allow the sort block to move in an arc, with the flow cell nozzle at the top of the arc. By moving the sort block slightly the droplet stream may be centered between the deflection plates. It should be noted that side-to-side positioning is more critical than front-to-back positioning. The present design allows all elements of the sort block, including the associated collection containers and laser/camera monitoring system to be repositioned, moving in an arc as a single unit. This keeps all elements of the sort block in alignment while ensuring alignment of the droplet stream centered between the deflection plates such that undeflected droplets flow into the aspiration collection fin.

Other methods for repositioning the sort block are also available. For example, bolts securing the sort block to a frame of a flow cytometer may allow the block to be repositioned along one axis, allowing side-to-side repositioning. The sort block could also be mounted on a stage allowing the sort block to be repositioned relative to the direction of the droplet stream. This stage could allow only angular repositioning (e.g. α angling) or could allow x-y-z and α, θ movement. The sort block preferably may move in an arc with the droplet stream source (the nozzle) at the top of the arc. This allows the droplet stream to be centered in the sort block. The sort plates are maintained at a fixed distance on either side from the droplet stream. The undeflected droplets flow into the open end of the collection fin.

Returning to FIG. 2A, on top of sort block body 20 surface 24 provides an area where the flow cell, droplet generator (e.g. piezioelectric collar, spray nozzle) and droplet charging system are mounted. The generated droplets are directed between electrostatic charge plates 22. The plates are charged by terminals 27 connected to wires 26. The charges placed on the droplets 22 (generally 100–200 volts to either side of the ground in amplitude) allow deflection by the charged plates (generally charged to 2000 to 6000 V). As noted, by alteration of the charge of the plates or charge on the droplets, the degree of deflection of the droplets may be altered. The droplets may be sorted into four deflected sort angles directing the droplets for four sort containers.

With reference to FIG. 3, the particles, as they fall, pass rear window hole 28 and perpendicular side window hole 29. An illumination source (e.g. laser) is positioned to shine through the window placed in window hole 29. A camera viewing the flow stream through window hole 28 is able to capture images of the illuminated flow stream. This allows determination of error (e.g. if the droplet flow pattern suddenly charges.

Returning to FIG. 2A, side window 42 is held against O-ring 40 at the side window hole by retainer 44. In a similar manner rear window 48 is pressed against O-ring 50 by retainer 46. Each O-ring 40, 50 seals the window to sort block body 20, preventing aerosol escape.

The droplet stream flows through the sort chamber of sort block 20, through opening 70, and into the containers 32 held within container retention well 34 on collection container holder 30. An O-ring on the bottom the sort block 20 seals sort block 20 to collection container holder 30, again preventing aerosol escape.

With reference to FIG. 3, on the sort block body 20 the actuator arm holding the actuator would be inserted through hole 25. In this device an aspirator draws air through the aerosol collector. The volume of air evacuated by the aspirator would need to be replenished within the sort block. It is possible that minor leaks from the flow cell, droplet generator, or droplet charging system would be sufficient to replace evacuated air. However, it is preferred that the system would be sealed against such leaks. In that case a circuitous air intake 72 would be patterned into the top of sort block 20, as seen in FIG. 3. A filter may be used with air intake 72 (e.g. a submicron filter) to ensure that contaminating particles do not enter the sort block and aerosol does not leave the sort block.

The aspiration unit inserted into the sort block through hole 25 in FIG. 3 is illustrated in FIGS. 4 and 5. Frame 110 is mounted on the rear of the sort block by screws 112 having locking washers 114. Attached to frame 110 by nut 140 is actuator 138. Actuator 138 may be a pneumatic cylinder or other similar device allowing rapid extension of associated actuator arm 142. Mounted on the end of arm 142 is particle collector 144. This device is comprised of a central fin 146 and two side baskets 150, 152. Fin 146 has an open fin top 148. An aspiration force from an aspiration source is introduced through tube 160 attached by fitting 162 to arm 142. Arm 142 has a channel leading into fin 146. Separate drain holes at the bottom of baskets 150, 152 allow the aspiration force to be drawn through baskets 150, 152 when they are positioned in the flow stream.

As shown in FIGS. 4 and 5, the fin and baskets are used as a single unit, with the baskets affixed to either side of the fin. In alternative embodiments, the fin may be in a fixed position while the baskets extend and retract on either side of the fin.

In FIG. 6, a cross section of the fin illustrates the path of the aspiration force. The actuator arm is attached to the fin and basket device at port 178. The arm is retained on the basket such that an aspiration tube running through the arm enters port 178 where it is fitted and sealed. The aspiration force travels through tube 176 to openings 172, 174. The use of a tube having an opening at the front and back of the fin aids in drawing aerosol and droplets into the fin and prevents backsplash from escaping the fin. Here the vacuum force draws air through interior space 170 of fin 146. This allows the aspiration force to be transmitted out open fin end 148, providing an aspiration force in the direction of droplet generation. Openings 172 extends into the baskets flanking fin 146. The walls of the baskets are angled towards opening 172 to direct fluid collected by the baskets to flow to opening 172.

Returning to FIGS. 4 and 5, also mounted on frame 110 is camera 128. Camera 128 is mounted on frame 110 by positioning washers 134, 136 on either side of slot 136 and securing bolt 132 into camera body 128. When frame 110 is mounted on the sort block body, lens 130 will be focused to collect images from window 50 shown in FIGS. 1A and 1B on the back of the sort block body 20.

One or more filters may be used in front of lens 130 enhance image capture. In FIGS. 4 and 5, filters 124 and 126 are mounted side by side on filter holder 122. Filter holder 122 is attached by arm 121 to actuator 120. Actuator 120 is operated to move filter holder 122 such that a selected one of filters 124, 126 may be positioned in front of lens 130. Actuator 120 is attached frame extension 116 by nut 118. Although the present filter system is pictured with two filters, a greater number of filters could be employed.

With reference to FIG. 1A, the cross-section of FIG. 2B is shown with the added elements of the camera, filters, and aspiration device also shown in cross section. In cross section block 20 and associated block face 10 define the interior chamber through which sorted cells pass (indicated by arrow A). Lens 130 of camera 128 is positioned to aim through filter 124 (held on filter holder 122), through window 50 onto the interior of the sort block. An illumination source, such as a laser beam, directed orthogonally to the camera, illuminates the droplets as they travel through the interior chamber of the sort block. These droplets are monitored by camera 128 allowing early detection of sort stream interruption and possible error.

Camera 128 is secured by bolt 124 onto frame 110. Frame 110 is secured by screws or bolts to sort block 20. Actuator 138 is also secured to frame 110 by nut 140. Actuator 138 is able to move arm 142 into an engaged and non-engaged position. In FIG. 1A the arm is in a non-engaged position.

Mounted at the end of arm 142 is particle collector 144. Fin 146 extends from particle collector 144 into the path of droplets flowing through the sort block. Fin 146 must extend into the sort block at least far enough so that it is able to collect unsorted droplets (i.e. droplets that have not been deflected by the sort system). This location will depend on the placement of the droplet generator but will generally be in the middle of the sort chamber. In the illustrated embodiment, the far edge of fin 146 extends to the edge of the plane made by the back of block face 10. This may be preferred for generating an even laminar air flow in the interior chamber in the sort block. In the retracted position (first position) the side collection baskets (not shown in FIG. 1A) are not in the path of the droplet stream. A vacuum source from tube 160 travels through a tube in arm 142, through tube 176 and produces a suction source that draws undeflected droplets and any aspirated liquid into the fin while allowing deflected droplets to pass the fin on either side. The deflected droplets pass through hole 70 into the collection containers below the sort block.

If a system sensor indicates an error (e.g. error detection by camera 128, electronics monitoring, pressure monitoring, computer system error, manual determination etc.) the collection basket is extended to collect all droplets and liquid in the sort block and prevent this liquid from passing through opening 70 into collection containers. In FIG. 1B the cross-section of FIG. 1A is shown with arm 142 extended by actuator 138 and particle collector 144 extending into the interior of the sort block chamber. Fin 146 extends into notch 14 on block face 10. The open top of fin 146 extends back into particle collector 144 sufficiently far so that even in the extended position the open top of fin 146 is able to collect aerosol or droplets flowing in the direction of arrow A. The suction draws aerosol and droplets from the interior of the sort block and into suction line 160 suction line 160 may flow to a recovery container allowing subsequent recovery and resorting of particles collected by the fin or the fin and basket. The collection baskets extend from the sides of fin 146 and ensure that no liquid is able to pass through opening 70 and into collection containers. The baskets are wide enough to block all of opening 70, preventing any liquid from reaching the collection containers when the actuator is engaged in this second position.

It should be appreciated that the present invention may be employed in a number of different ways. The present sort block may be used with an integrated collection container holder, as illustrated. Additionally, the sort block may be used alone and mounted over a cabinet. The cabinet could be similar to the one described in PCT publication WO 01/85088 A1. The block would be mounted onto the cabinet over an opening and the bottom O-ring on the sort block would ensure that aerosol could not escape from area where the sort block is mounted to the cabinet. The opening would lead to collection containers.

When the sorted particles enter into the cabinet the particles could be directed to any of a number of containers. For example, a multiwell plate could be placed on an x,y directionally movable platform within the cabinet. The sorted particles could enter receptacles on a multiwell plate held on the platform. A computer control could move the plate along the x,y axis when directed (e.g. to collect particles from a new sample to be sorted). The use of a standard size 96 well microplate would allow subsequent analysis of collected particles on a number of different automated systems. In addition, robotic handling of the plates of collected particles could reduce labor needs and increase system throughput.

If a cabinet is used, negative pressure would be maintained in the cabinet to ensure any escaped aerosols would be collected. Air would be introduced through a sub-micron, filtered intake and evacuated by an aspirator. Even with the use of this cabinet, the area required to be enclosed is greatly reduced and access to system components greatly enhanced by the use of the instant invention.

In another possible embodiment, the aspiration unit of the present invention could be equipped on a flow cytometer that uses a more open system architecture. The aspiration unit would use the fin to extend into the flow stream to collect undeflected droplets. The actuator could extend the baskets to collect deflected particles when required. This component alone could be used with a number of systems, including systems in which the entire cytometer is contained within a cabinet to contain aerosols. The use of the fin would allow for a laminar flow from the sort nozzle to the fin opening, collecting aerosol and unsorted droplets. Thus, the fin and basket aspirator and flow stream collected may be used as an element for a number of flow cytometer systems to aspirate aerosol and prevent contamination of sorted droplets.

What is claimed is:

1. A cell sort block comprising:
   a block body, having an open top, an open bottom and an elongate interior chamber;
   a block face sealed over said body to enclose on four sides the interior chamber; said chamber having a top chamber opening through which droplets may be introduced in a flow stream into said chamber and an open chamber bottom through which droplets leave the chamber and flow into collection containers;
   a particle deflector disposed to deflect charged droplets that pass through said chamber;

a fin having an open fin top facing the housing top opening and a closed fin bottom defining a fin slot, said fin located between the particle deflector and the bottom opening and extending into a depth of said interior chamber such that deflected particles are deflected to one of two sides of said fin and undeflected particles pass into said open fin top; and an aspiration source evacuating air through said fin slot, said aspiration source providing a negative air pressure within said chamber moving air within said interior chamber into said open fin slot.

2. The sort block of claim 1, further comprising a circuitous intake path on a surface of said block body top allowing a gas to move from outside the sort block to inside the interior chamber.

3. The sort block of claim 1, wherein the block face is clear.

4. The sort block of claim 1, further including an o-ring between said block face and said block body.

5. The sort block of claim 1, wherein said fin is mounted on an actuator.

6. The sort block of claim 5, further comprising a pair of collection baskets mounted flanking the fin, wherein said actuator may move said collection baskets between a first position and a second position wherein in said first position said baskets are positioned out of the flow stream and in a second position said baskets are positioned in the flow stream blocking flow of droplets through said open chamber bottom.

7. The sort block of claim 6, further including an error sensor, wherein when an error is sensed by said error sensor the actuator is activated to move the fin and collection baskets to the second position, thereby collecting the flow stream emanating from the flow cell.

8. The sort block of claim 7, wherein said error sensor includes a laser directed into the flow stream and a camera monitoring the flow stream.

9. The sort block of claim 8, further including at least one filter positioned in front of a lens of said camera.

10. The sort block of claim 9, wherein said at least one filter comprises two filters disposed on a filter holder and said block further includes a filter actuator joined to said filter holder whereby actuation of said filter actuator moves a different filter in front of the camera.

11. The sort block of claim 7, wherein said error sensor is one of a group consisting of a flow cell monitor, a pressure monitor and a computer error sensor.

12. The sort block of claim 6, wherein said baskets are affixed to said fin such that both the baskets and the fin move as a single unit.

13. The sort block of claim 6, wherein the collection baskets each have a hole within the collection basket in communication with the aspiration source.

14. The sort block of claim 13, wherein collected droplets are recovered by a recovery line feeding to a recovered liquid container.

15. The sort block of claim 1, further comprising a collection container holder joined to said sort block body such that a plurality of containers placed in said collection container holder are held in the path of deflected droplets.

16. The sort block of claim 15, further comprising an o-ring between the block housing and the collection container holder such that an air-tight seal between said block housing and said collection container holder is formed.

17. The sort block of claim 1, further including a pivotable mount, said mount allowing the sort block to be mounted on a frame and pivot in relation to the position of a fixed flow cell.

18. A device for use with a sorting flow cytometer, said cytometer having a flow cell for analysis of particles, a droplet generator producing droplets containing said particles, a charging system and deflection plates for sorting charged droplets in a flow stream, an enclosed block body having an interior chamber through which said flow stream of droplets pass and a plurality of collection containers for collecting deflected droplets at an end of said interior chamber, the device comprising:

a fin having an open end and a closed end, said fin positioned between said deflection plates and said collection containers and having said open end facing said deflection plates said open end oriented to collect undeflected droplets;

an aspirator connected to said fin such that air in front of said open end is evacuated through said open end;

a pair of baskets flanking said fin, said baskets having an open end and a closed end, wherein a front end of said fin extends beyond said baskets;

an actuator arm onto which said fin and baskets are mounted;

an actuator mechanically linked to said actuator arm such that said actuator arm may position said fin and baskets in a retracted position and an extended position, wherein when said device is used in said sorting flow cytometer in said retracted position said open end of said fin collects a central stream of unsorted particles and said baskets do not collect sorted particles, and when said fin end baskets are in an extended position said baskets are positioned to collect deflected particles while said fin continues to collect undeflected particles, thereby blocking droplets from flowing into said collection containers.

19. The device of claim 18, wherein said device further includes an error sensor, wherein when said error sensor detects a flow cytometer error said actuator activates and moves said fin and basket to the extended position.

20. The device of claim 19, wherein said sensor includes a light source illuminating the flow stream and a camera viewing droplets illuminated by said light source, wherein a change in droplet flow rate may be detected by said camera triggering actuator movement to said extended position.

21. The device of claim 19, wherein said sensor is selected from a group comprising a pressure sensor, an power flow sensor, an optical sensor, and a computer error sensor.

22. A flow cytometer cell sorting device comprising:

an elongate block body enclosing three sides;

a block face fit onto said block body enclosing a fourth side to define a block chamber having an open top end and an open bottom end;

an electrostatic particle deflector disposed to deflect charged droplets in a droplet stream introduced through said block chamber producing a stream of undeflected droplets and one or more streams of deflected droplets;

a holder for droplet collection containers joined to said block body, said holder designed to hold at least two collection containers at a location to receive deflected droplets;

a fin disposed in said chamber between said deflector and said holder, the fin having a closed fin bottom and an open fin top facing said particle stream;

a pair of baskets flanking said fin;

an aspiration source drawing air through said open fin top;

an actuator arm onto which said fin and baskets are mounted; and an actuator mechanically linked to said actuator arm such that said fin and baskets may be moved between a first and second position, wherein in said first position said fin collects undeflected droplets and aerosol in said open end while deflected droplets pass to the collection container and wherein in said second position said fin is further extended into a notch on said block face and said baskets are extended into said block chamber such that deflected, non-deflected and aerosol are collected and droplets do not pass to said collection containers; and a system for actuating said actuator.

23. The device of claim 22, wherein said system for actuating said actuator includes an error sensor selected from the group comprising an optical error sensor, an electronics monitoring sensor, a pressure sensor and a computer error sensor.

24. The device of claim 22, wherein said system for actuating said actuator includes a manually activated switch in which a user activates the actuator.

25. The device of claim 22, further including a first o-ring between said block face and said block body and a second o-ring between said block body and said collection container holder.

26. The device of claim 22, further including a recovery container associated with said aspiration source such that droplets and aerosol collected by said baskets and fin are drawn into said recovery container.

27. The device of claim 22, wherein said block face is transparent.

* * * * *